United States Patent [19]

Abbott et al.

[11] 4,293,482

[45] Oct. 6, 1981

[54] A-30912A NUCLEUS

[75] Inventors: Bernard J. Abbott, Greenwood; David S. Fukuda, Brownsburg, both of Ind.

[73] Assignee: Eli Lilly and Company, Indianapolis, Ind.

[21] Appl. No.: 181,029

[22] Filed: Aug. 25, 1980

Related U.S. Application Data

[63] Continuation-in-part of Ser. No. 103,017, Dec. 13, 1979, abandoned.

[51] Int. Cl.$^3$ .................... C07C 103/52; H61K 37/00; C12P 21/04
[52] U.S. Cl. ............................ 260/112.5 R; 424/177; 435/71
[58] Field of Search ................... 435/71; 260/112.5 R; 424/177

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 834289 | 7/1975 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |
| 38-405867 | 7/1963 | Japan | 260/112.5 R |
| 568386 | 4/1972 | Switzerland | 260/112.5 R |

OTHER PUBLICATIONS

T. Kato et al., J. Antibiotics 29 (12), 1339-1340 (1976).
S. Chihara et al., Agr. Biol. Chem. 37 (11), 2455-2463 (1973).
S. Chihara et al., Ibid. 37 (12), 2709-2717 (1973).
S. Chihara et al., Ibid. 38 (3), 521-529 (1974).
S. Chihara et al., Ibid. 38 (10), 1767-1777 (1974).
T. Suzuki et al., J. Biochem. 56 (4), 335-343 (1964).
J. M. Weber et al., J. Antibiotics 31 (4), 373-374 (1978).
J. Shoji et al., J. Antibiotics 28, 764-769 (1975).
J. Shoji et al., Ibid. 29 (4), 380-389 (1976).
J. Shoji et al., Ibid. (12), 1268-1274 (1976).
J. Shoji et al., Ibid. (12), 1275-1280 (1976).
F. Benz et al., Heln, Chim. Acta. 57, 2459 (1974).
C. Keller-Juslen, et al., Tetrahedron Letters, 4147-4150, 1976, vol. 46.
R. Traber et al., Helv. Chim. Acta. 62, 1252 (1979).

*Primary Examiner*—Delbert R. Philips
*Attorney, Agent, or Firm*—Nancy J. Harrison; Arthur R. Whale

[57] ABSTRACT

A-30912A nucleus, which is prepared by enzymatic deacylation of an antibiotic selected from A-30912 factor A, tetrahydro-A-30912A, and aculeacin A using an enzyme produced by the Actinoplanaceae, preferably by *Actinoplanes utahensis*. A-30912A nucleus and salts thereof are useful intermediates to prepare new semisynthetic antifungal agents.

22 Claims, 1 Drawing Figure

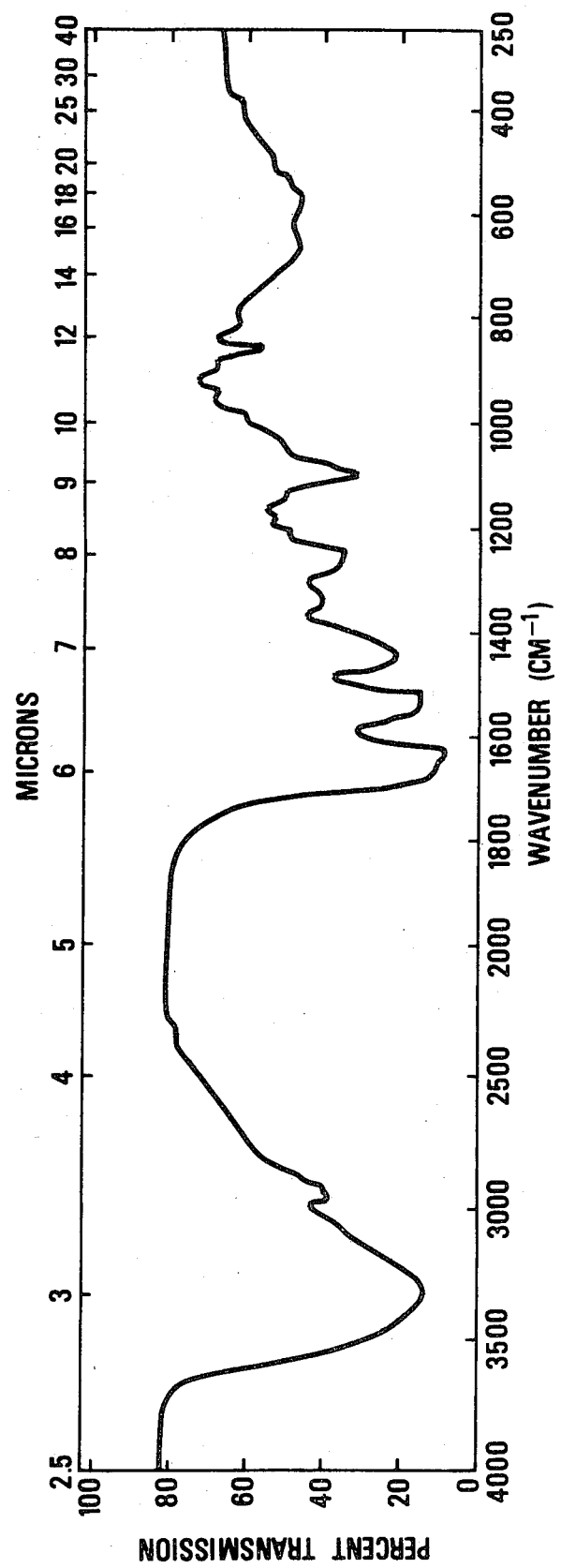

A-30912A NUCLEUS

CROSS-REFERENCE TO RELATED APPLICATION

This application is a continuation-in-part of application Ser. No. 103,017, filed Dec. 13, 1979, now abandoned.

SUMMARY OF THE INVENTION

This invention relates to A-30912A nucleus of the formula:

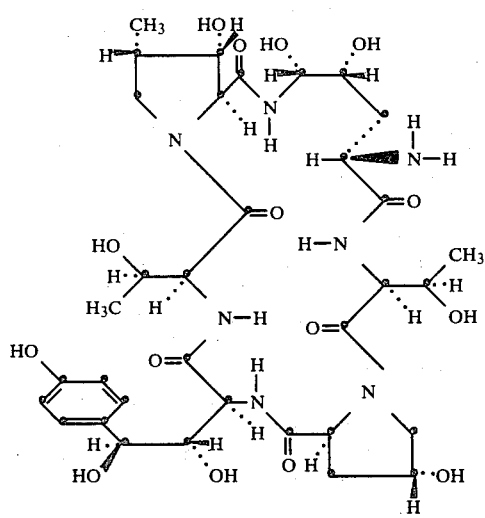

and acid-addition salts thereof. Throughout this application, the cyclic peptide formulas, such as formula 1, assume that the amino acids represented are in the L-configuration. A-30912A nucleus and its salts are useful as intermediates in the preparation of semisynthetic antifungal agents.

In another aspect, this invention relates to a method of deacylating the cyclic peptide antibiotics A-30912 factor A, tetrahydro-A-30912 factor A, and aculeacin A. These antibiotics have a common cyclic peptide nucleus, but each has a different fatty acid side chain. We have discovered a method of enzymatically removing the fatty acid side chain to give the cyclic peptide nucleus. For convenience herein, this nucleus will be called A-30912A nucleus. The method comprises exposing the antibiotic in an aqueous medium to an enzyme produced by a microorganism of the family Actinoplanaceae until substantial deacylation is accomplished.

A preferred method of this invention comprises using an enzyme produced by the microorganism *Actinoplanes utahensis* NRRL 12052 to cleave the fatty acid side chain. Deacylation is ordinarily accomplished by adding the appropriate antibiotic to a culture of *A. utahensis* and permitting the culture to incubate until deacylation is accomplished. The A-30912A nucleus thereby obtained is separated from the fermentation broth by methods known in the art. This nucleus is useful in that it can be reacylated to provide new antibiotic substances.

DESCRIPTION OF THE DRAWING

The infrared absorption spectrum of A-30912A nucleus in KBr disc is presented in the accompanying drawing.

DETAILED DESCRIPTION OF THE INVENTION

Field of the Invention

The A-30912A nucleus of this invention is obtained by deacylating a peptide antibiotic selected from the group consisting of A-30912 factor A, tetrahydro-A-30912 factor A, and aculeacin A.

A. A-30912 Factor A

A-30912 factor A is a factor of the A-30912 complex which also contains factors B, C, D, E, F, and G. The A-30912 complex and individual factors A through G are disclosed by Marvin M. Hoehn and Karl H. Michel in U.S. Pat. No. 4,024,245. A-30912 factor A is identical to antibiotic A-22082 which is described by Calvin E. Higgens and Karl H. Michel in U.S. Pat. No. 4,024,246.

Since the issuance of U.S. Pat. Nos. 4,024,245 and 4,024,246, it has been found that A-30912 factor A is identical to the antibiotic echinocandin B [see F. Benz et al., *Helv. Chim. Acta* 57, 2459–2477 (1974) and Swiss Pat. No. 568,386]. Antibiotic SL 7810/F has also been identified as echinocandin B [C. Keller-Juslen, et al., *Tetrahedron Letters* 1976 (46), 4147–4150, and Belgium Pat. No. 834,289 (Derwent Abstract 30159X)].

Keller-Juslen, et al., proposed structure 2 for this antibiotic:

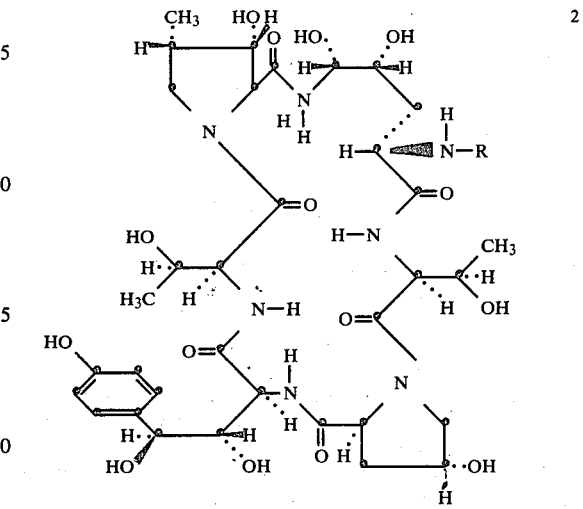

wherein R=linoleoyl

B. Tetrahydro-A-30912 Factor A

Tetrahydro-A-30912 factor A (tetrahydro-SL 7810/F; tetrahydroechinocandin B), which is described in Belgium Pat. No. 834,289 (Derwent Abstract 30159X) and by F. Benz et al., *Helv. Chim Acta* 57, 2459–2477 (1974), has structure 2 wherein R is stearoyl. For convenience herein, this material will be called tetrahydro-A-30912A.

C. Aculeacin A

Aculeacin A is a component of the aculeacin complex which consists of one major component (aculeacin A) and six minor components (aculeacins B, C, D, E, F, and G). The aculeacin components are described by K. Mizuno, et al., in U.S. Pat. No. 3,978,210. As is discussed in Belgian Pat. No. 859,067 (Derwent Abstract 25187A/14), aculeacin A probably has the same cyclic peptide structure as tetrahydro-A-30912A except that the stearoyl side chain is replaced by palmitoyl.

A-30912A Nucleus

The novel cyclic peptide nucleus of this invention, i.e., the nucleus of A-30912 factor A (echinocandin B, SL 7810/F), tetrahydro-A-30912 factor A, and aculeacin A has the structure shown in formula 1.

This nucleus (A-30912A nucleus) is a white amorphous material which is soluble in solvents such as water, dimethylformamide, dimethyl sulfoxide and methanol and which is insoluble in solvents such as chloroform, toluene, and diethyl ether.

A-30912A nucleus has an empirical formula of $C_{34}H_{51}N_7O_{15}$ and a molecular weight of 797.83.

The infrared absorption spectrum of A-30912A nucleus in KBr disc is shown in the accompanying drawing. The following absorption maxima are observed: 3340 broad (OH, H-bonded), 2970, 2930, and 2890 (CH stretch, aliphatic in $CH_3$, $CH_2$, CH groups), 1660 and 1625 (several carbonyls C=O), 1510–1550, 1430–1450 (CH wag), 1310–1340, 1230–1260, 1080, 835, 650 broad, and 550 broad $cm^{-1}$.

Electrometric titration of A-30912A nucleus in 66% aqueous dimethylformamide indicates the presence of a titratable group with a $pK_a$ value of about 7.35 (initial pH 7.32).

A-30912A nucleus can be separated by highperformance liquid chromatography (HPLC). A-30912A nucleus has an approximate retention time (k') of 11.52 minutes when separated by HPLC using the following conditions:

Column: 4×300 mm
Packing: silica gel/$C_{18}$
Solvent: ammonium acetate:acetonitrile:water (1:2:97)
Flow Rate: 3 ml/min
Pressure: 2500 psi
Detector: variable wavelength UV at 230 nm
Sensitivity: 0–0.4 A.U.F.S.

Because the A-30912A nucleus contains an amino moiety, it may exist in the form of salts. Such salts are also useful as intermediates and for purification purposes. The pharmaceutically acceptable salts of the A-30912A nucleus are especially useful because purification of final products will be minimized. "Pharmaceutically acceptable" salts refer to those salts in which the toxicity of product as a whole toward warm-blooded animals is not increased.

Acid addition salts of A-30912A nucleus may be formed by standard reaction procedures with an inorganic or organic acid. Representative inorganic and organic acids include hydrochloric, hydrobromic, hydriodic, sulfuric, phosphoric, acetic, benzoic, sulfamic, tartaric, citric, maleic, succinic, ascorbic, glycolic, lactic, fumaric, palmitic, cholic, pamoic, mucic, D-glutamic, d-camphoric, glutaric, phthalic, lauric, stearic, salicylic, methanesulfonic, benzenesulfonic, sorbic, picric, cinnamic, and other suitable acids.

Preparation of A-30912A Nucleus

A. Preparation of the Substrate

The A-30912A nucleus of this invention may be prepared from A-30912 factor A, tetrahydro-A-30912 factor A, or aculeacin A. These substrates may be supplied as purified materials, but it is not essential that they be purified. Thus, for example, A-30912 complex, wherein A-30912 factor A is the major component, may be used as a substrate to prepare A-30912A nucleus.

1. A-30912 Factor A

A-30912 factor A may be produced by fermentation of: (1) a strain of *Aspergillus rugulosus* NRRL 8113 as described in U.S. Pat. No. 4,024,245; (2) a strain of *Aspergillus nidulans* NRRL 8112 as described in U.S. Pat. No. 4,024,246; (3) a strain of *Aspergillus nidulans* var. *echinulatus* A-32204, NRRL 3860 as described in Swiss Pat. No. 568,386; or (4) a strain of *Aspergillus rugulosus* NRRL 8039 as described in Belgian Pat. No. 834,289.

A method for preparing A-30912 factor A is also described in a co-pending application of LaVerne D. Boeck and Ralph E. Kastner entitled METHOD OF PRODUCING THE A-30912 ANTIBIOTICS, Ser. No. 126,078, filed Mar. 3, 1980, a continuation-in-part of application Ser. No. 46,744, filed June 8, 1979 (now abandoned), which is incorporated herein by reference. This method uses a new culture which has been named *Aspergillus nidulans* var. *roseus*.

A subculture of this microorganism has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of *A. nidulans* var. *roseus* NRRL 11440 is used to produce A-30912 factor A, a complex of factors is obtained which for convenience is called the A-42355 antibiotic complex. A-30912 factor A is the major factor of the A-42355 antibiotic complex. A-30912 factors B, D and H are minor factors of the A-42355 complex. A-30912 factor H is further described in a co-pending application of Karl H. Michel entitled ANTIBIOTIC A-30912 FACTOR H. Ser. No. 117,739, filed Feb. 1, 1980, a continuation-in-part of application Ser. No. 46,875, filed June 8, 1979 (now abandoned).

As discussed in the co-pending application of Karl. H. Michel entitled RECOVERY PROCESS FOR A-30912 ANTIBIOTICS, Ser. No. 103,014 filed Dec. 13, 1979, reversed-phase high performance, low pressure liquid chromatography (HPLPLC) using silica gel/$C_{18}$ adsorbent is a preferred method for the final purification of A-30912 factor A. In this method (see Example 6), A-30912 complex or A-42355 complex (obtained, for example, by extraction of the whole broth or mycelia with methanol and chloroform), dissolved in solvent, is placed on a column equilibrated with the same solvent. The column is then eluted with the solvent. Methanol:-water:acetonitrile (7:2:1) is a preferred solvent system. Fractions collected are monitored by *Candida albicans* bioautography and/or by UV (based on relative retention times). Fractions containing A-30912 factor A are combined. It is sometimes necessary to carry out an additional chromatographic separation in order to obtain A-30912 factor A in purified form.

The individual A-30912 factors can be identified by the use of thin-layer chromatography (TLC). Silica gel is a preferred adsorbent.

The $R_f$ values of A-30912 factors A-G, using silica gel (Merck, Darmstadt) TLC, a benzene:methanol (7:3) solvent system, and *Candida albicans* bioautography are given in Table I.

TABLE I

| A-30912 Factor | R_f Value |
| --- | --- |
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table II.

TABLE II

| A-30912 Factor | R_f Values - Solvent Systems | | | |
| --- | --- | --- | --- | --- |
| | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

A-30912 factors A, B, D and H can also be identified by analytical HPLPLC using the following conditions:

| | |
| --- | --- |
| Column: | glass, 0.8 × 15.0 cm |
| Packing: | Nucleosil ® 10-C$_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table III.

TABLE III

| A-30912 Factor | Retention Time (seconds) |
| --- | --- |
| A | 792 |
| B | 870 |
| H | 990 |
| D | 1,140 |

2. Tetrahydro-A-30912A

Tetrahydro-A-30912A is prepared from A-30912 factor A by standard hydrogenation techniques, carrying out the reduction until both double bonds of the linoleoyl side chain have been reduced.

3. Aculeacin A

Aculeacin A is prepared by fermentation of a strain of *Aspergillus aculeatus* NRRL 8075 as described in U.S. Pat. No. 3,978,210 which is incorporated herein by reference.

B. Preparation of the Enzyme

1. The Producing Microorganism

The enzyme which is useful for deacylation of A-30912 factor A, tetrahydro-A-30912A, and aculeacin A is produced by certain microorganisms of the family Actinoplanaceae, preferably the microorganism *Actinoplanes utahensis* NRRL 12052.

The enzyme may be the same enzyme which has been used to deacylate penicillins; this work is described by Walter J. Kleinschmidt, Walter E. Wright, Frederick W. Kavanagh, and William M. Stark in U.S. Pat. No. 3,150,059 (issued Sept. 22, 1964). Although a preferred method of cultivating *A. utahensis* NRRL 12052 to produce this enzyme is described in Example 1, it will be recognized by those skilled in the art that other methods may be used.

The Actinoplanaceae are a comparatively recent family of microorganisms of the order Actinomycetales. First described by Dr. John N. Couch, this family was established in 1955 [*J. Elisha Mitchell Sci. Soc.* 71, 148–155 (1955)]. The characteristics of the family and of many individual genera are found in "Bergey's Manual of Determinative Bacteriology", 8th ed., R. E. Buchanan and N. E. Gibbons, Eds., The Williams & Wilkins Co., Baltimore, Md., 1974, pages 706–723. Ten genera have thus far been distinguished: I. Actinoplanes (the type genus and thus far the most common genus); II. Spirillospora; III. Streptosporangium; IV. Amorphosporangium; V. Ampullariella; VI. Pilimelia; VII. Planomonospora; VIII. Planobispora; IX. Dactylosporangium; and X. Kitasatoa.

Some of the species and varieties which have been isolated and characterized so far are: *Actinoplanes philippinensis, Actinoplanes armeniacus, Actinoplanes utahensis*, and *Actinoplanes missouriensis; Spirillospora albida; Streptosporiangium roseum, Streptosporangium vulgare, Streptosporangium roseum* var. *hollandensis, Streptosporangium album, Streptosporangium viridialbum, Amorphosporangium auranticolor, Ampullariella regularis, Ampullariella campanulata, Ampullariella lobata, Ampullariella digitata, Pilimelia terevasa, Pilimelia anulata, Planomonospora parontospora, Planomonospora venezuelensis, Planobispora longispora, Planobispora rosea, Dactylosporangium aurantiacum*, and *Dactylosporangium thailandense*.

The genus Actinoplanes is a preferred source of the enzyme which is useful for this invention. Within the genus Actinoplanes, the species *Actinoplanes utahensis* is an especially preferred source.

Cultures of representative species are available to the public from the Northern Regional Research Center, address supra, under the following accession numbers:

| | |
| --- | --- |
| *Actinoplanes utahensis* | NRRL 12052 |
| *Actinoplanes missouriensis* | NRRL 12053 |
| *Actinoplanes sp.* | NRRL 8122 |
| *Actinoplanes sp.* | NRRL 12065 |
| *Streptosporangium roseum* var. *hollandensis* | NRRL 12064 |

*A. utahensis* NRRL 12052 was derived from a parent culture which was also deposited with the American Type Culture Collection (ATCC), 12301 Parklawn Drive, Rockville, Md. 20852 (*A. utahensis* ATCC 14539). The *A. utahensis* ATCC 14539 culture may also be used as a source of the enzyme.

*A. missouriensis* NRRL 12053 was derived from a culture which was also deposited with ATCC (*A. missouriensis* ATCC 14538) and which is another source of the enzyme. The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. This procedure is described in Sect. E. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. linoleoyl, stearoyl, or palmitoyl) to restore activity.

2. Conditions for Enzyme Production

Production of the enzyme occurs under conditions satisfactory for growth of the Actinoplanaceae, i.e., a temperature between about 25° and about 30° C. and a pH of between about 5.0 and about 8.0, with agitation and aeration. The culture medium should contain (a) an assimilable carbon source such as sucrose, glucose, glycerol, or the like; (b) a nitrogen source such as peptone, urea, ammonium sulfate, or the like; (c) a phosphate source such as a soluble phosphate salt; and (d) inorganic salts found generally to be effective in promoting the growth of microorganisms. An effective amount of the enzyme is generally obtained in from about 40 to about 60 hours after the beginning of the growth cycle and persists for some time after the effective growth has been reached. The amount of enzyme produced varies from species to species of the organism and in response to different growth conditions.

As will be apparent to those in the field, the microorganisms, such as *Actinoplanes utahensis* NRRL 12052, which produce the enzyme are subject to variation. For example, artificial variants and mutants of these strains may be obtained by treatment with various known mutagens such as ultraviolet rays, X-rays, high-frequency waves, radioactive rays, and chemicals. All natural and artificial variants and mutants which are obtained from the Actinoplanaceae and which produce the enzyme may be used in this invention.

C. Deacylation Conditions

The substrate used as the starting material is preferably added to the culture of Actinoplanaceae after the culture has been incubated for at least about 48 hours. The concentration of substrate in the conversion medium can vary widely. For maximum use of the enzyme and for substantially complete deacylation within a 24-hour period, however, the concentration of substrate will generally range from about 0.5 to about 1.4 mg/ml. Lower concentrations can be used, but may not make maximum use of the enzyme; higher concentrations can also be used, but the substrate may not be completely deacylated unless the fermentation time is extended.

Conversion of the substrate antibiotic to A-30912A nucleus according to this invention proceeds best when the pH of the fermentation medium is maintained in the range of from about 6.0 to about 7.0. At pH 6 or below, deacylation proceeds slowly; as pH values move above pH 6.0, both the substrate and the nucleus which is formed are increasingly less stable. For maximum stability, a pH of 6.0 is preferred; but at pH 6.0 the deacylation will occur less rapidly (about 30 to 36 hours). For more rapid deacylation (about 24 hours) without major losses, a pH of about 6.5 is preferred. In stirred fermentors the pH may be controlled by sensor controllers. Where this is impractical, such as in flask fermentors, pH may be controlled by adding 0.1 molar phosphate buffer to the medium prior to addition of the substrate.

After addition of the substrate, incubation of the culture should be continued for about 24 hours or longer. The purity of the substrate will affect the rate of deacylation. For example, substrate having a purity of greater than 50 percent is deacylated at a rate of about 0.8 to 1.2 mg/ml of antibiotic in 24 hours. When substrates of lower purity are used, the deacylation proceeds at a slower rate.

Multiple substrate feedings may be made. For example, in small tanks 0.3–0.5 mg/ml of antibiotic may be fed at 12-hour intervals for at least five additions, and in larger tanks 0.7 mg/ml may be fed twice.

The deacylation can be carried out over a broad temperature range, e.g. from about 20° to about 45° C. It is preferable, however, to carry out the deacylation at temperatures of from about 25° to about 30° C., especially at about 26° C., for optimum deacylation and stability of substrate and nucleus.

D. The Substrate

It is preferable, but not essential, to use purified antibiotic as the substrate. Because the purified substrate is soluble in lower alcohols or in 0.01 molar borate buffer, it can be handled more conveniently. Moreover, with purified substrate the deacylation proceeds more rapidly. Semipurified substrates containing as little as 4.8 percent of the starting antibiotic have been deacylated successfully. The deacylation rate decreases, however, as purity decreases. Furthermore, large amounts of the impurities generally present are not soluble in either alcohol or borate solution.

The substrate antibiotics have antifungal, but no antibacterial, activity. Thus, the substrate materials (especially those of low purity) may harbor bacterial cells or spores which could grow in the deacylation fermentation medium. Such contaminants can affect the deacylation reaction or the stability of the starting antibiotic or the product nucleus. It is important, therefore, that the substrates by sterile. Since preparations of lower purity are only partially soluble, they cannot be filter sterilized. Autoclaving destroys most of the substrate antibiotic (95–98 percent). It is preferable, therefore, to sterilize preparations with ethylene oxide treatment in a pressurized system. Using this sterilization method, starting material losses are only one to two percent.

E. Monitoring the Deacylation

The starting materials are antifungal antibiotics which are especially active against *Candida albicans*. For this reason an assay using *C. albicans* is preferable for determining quantities of substrate present. The A-30912A nucleus which is formed is water soluble, but is biologically inactive. Reduction in biological activity is, therefore, a quick, presumptive test for deacylation. Both broth samples and alcoholic extracts of the fermentation solids must be assayed because the substrate is only slightly soluble in the broth. Even when the substrate is added as an alcohol or borate solution, the major portion of substrate is present in the fermentation medium as a precipitate.

The amount of nucleus formed can be quantitated by HPLC analysis, using the system herein described.

F. Use of Resting Cells

An alternate method of deacylation involves removing the Actinoplanaceae cells from the culture medium, resuspending the cells in a buffer solution, and carrying out the deacylation as described in Sect. C. When this method is used, the enzymatically active mycelia can be re-used. For example, *A. utahensis* NRRL 12052 mycelia retain deacylase activity after storage for one month or longer under refrigeration (4°–8° C.) or in the frozen state (−20° C.). A preferred buffer solution is 0.1 molar phosphate buffer.

G. Immobilized Enzymes

Yet another method of carrying out the deacylation is to immobilize the enzyme by methods known in the art. (See, for example, "Biomedical Applications of Immobilized Enzymes and Proteins", Thomas Ming Swi Chang, Ed., Plenum Press, New York, 1977; Vol. 1.) The immobilized enzyme can then be used in a column (or other suitable type of reactor) to effect the deacylation.

In addition, the microorganism itself can be immobilized and used to catalyze the deacylation reaction.

Utility of the A-30912A Nucleus

The A-30912A nucleus and its acid-addition salts are useful intermediates in the preparation of semi-synthetic antifungal compounds. Useful antifungal compounds prepared from A-30912A nucleus are described in a copending application of Bernard J. Abbott and David S. Fukuda (Ser. No. 103,030) and in two copending applications of Manuel Debono (Ser. Nos. 103,149 and 103,012) all of which are entitled DERIVATIVES OF A-30912A NUCLEUS and which were filed Dec. 3, 1979. Continuation-in-part applications of these applications, with the corresponding Ser. Nos. 181,438, 181,030, and 181,442 are being filed herewith this even date.

The Abbott and Fukuda Derivatives

The compounds described in the Abbott and Fukuda application have the general formula shown in structure 3:

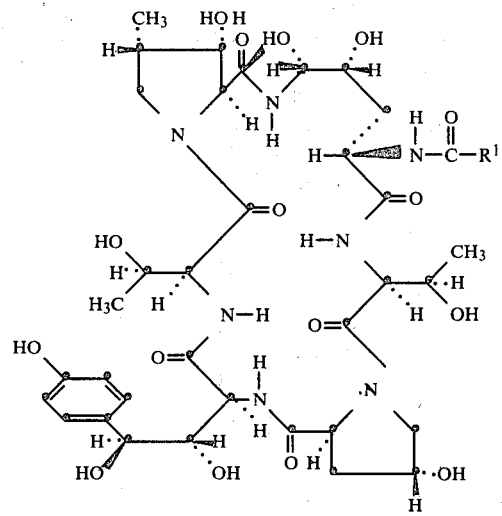

wherein $R^1$ is $C_6$–$C_{24}$ alkyl or $C_6$–$C_{24}$ alkenyl; provided that, when $R^1$ is alkyl, it cannot be n-tridecyl, n-tetradecyl, n-pentadecyl, or n-heptadecyl; and, when $R^1$ is alkenyl, it cannot be cis,cis-8,11-heptadecadienyl.

The term "alkyl" means a univalent, saturated, straight-chain or branched-chain hydrocarbon radical. The term "alkenyl" means a univalent, unsaturated, straight-chain or branched-chain hydrocarbon radical containing not more than three double bonds. The double bonds of the unsaturated hydrocarbon chain may be either in the cis or trans configuration. By "$C_6$–$C_{24}$" is meant a hydrocarbon (including straight and branched chains) containing from 6 to 24 carbon atoms.

The following are preferred embodiments of the compounds of formula 3:
(a) compounds wherein $R^1$ is alkyl of the formula $CH_3(CH_2)_n-$, wherein n is an integer from 5 to 23, provided that n cannot be 12, 13, 14, or 16;
(b) compounds wherein $R^1$ is alkyl of the formula $CH_3(CH_2)_n-$, wherein n is 10, 11, 15, 17, 18, 19, or 20;
(c) compounds wherein $R^1$ is alkyl of the formula

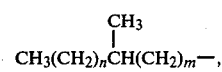

wherein n and m are each independently an integer from 0 to 21 provided that n+m must be no less than 3 and no greater than 21;
(d) compounds wherein $R^1$ is alkenyl containing one cis or trans double bond;
(e) compounds wherein $R^1$ is cis or trans alkenyl of the formula

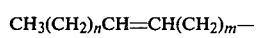

wherein n and m are each independently an integer from 0 to 21, provided that n+m must be no less than 3 and no greater than 21;
(f) compounds wherein $R^1$ is alkenyl containing two cis or trans double bonds;
(g) compounds wherein $R^1$ is cis or trans alkenyl of the formula

wherein n and p are each, independently, an integer of from 0 to 18 and m is an integer of from 1 to 19, provided that m+n+p must be no less than 1 and no greater than 19 and that $R^1$ cannot be linoleoyl; and (h) the compounds wherein $R^1$ is:
cis-$CH_3(CH_2)_5CH\!=\!CH(CH_2)_7$—
trans-$CH_3(CH_2)_5CH\!=\!CH(CH_2)_7$—
cis-$CH_3(CH_2)_{10}CH\!=\!CH(CH_2)_4$—
trans-$CH_3(CH_2)_{10}CH\!=\!CH(CH_2)_4$—
cis-$CH_3(CH_2)_7CH\!=\!CH(CH_2)_7$—
trans-$CH_3(CH_2)_7CH\!=\!CH(CH_2)_7$—
cis-$CH_3(CH_2)_5CH\!=\!CH(CH_2)_9$—
trans-$CH_3(CH_2)_5CH\!=\!CH(CH_2)_9$—
cis-$CH_3(CH_2)_7CH\!=\!CH(CH_2)_9$—
trans-$CH_3(CH_2)_7CH\!=\!CH(CH_2)_9$—
cis-$CH_3(CH_2)_7CH\!=\!CH(CH_2)_{11}$—
trans-$CH_3(CH_2)_7CH\!=\!CH(CH_2)_{11}$—
trans,trans-$CH_3(CH_2)_4CH\!=\!CHCH_2CH\!=\!CH(CH_2)_7$—
cis,cis,cis-$CH_3CH_2CH\!=\!CHCH_2CH\!=\!CHCH_2CH\!=\!CH\text{—}(CH_2)_7$—.

The Debono Derivatives

The compounds of the two Debono applications have the chemical structure depicted in formula 4:

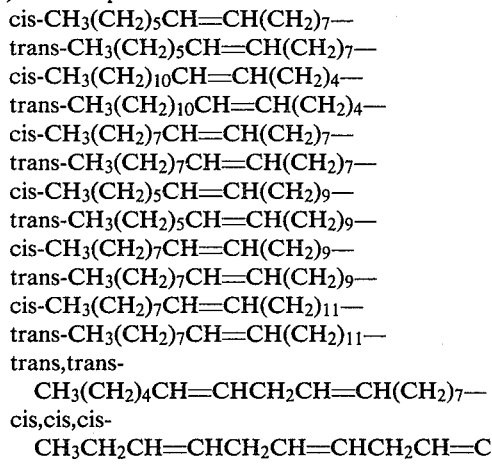

4

A. Debono Group I

In the group of derivatives described in Debono application Ser. No. 103,149, (Debono Group I), $R^1$ is an N-alkanoyl amino acyl group of the formula

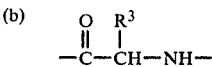

wherein:

W is a divalent aminoacyl radical of the formula:

(a) 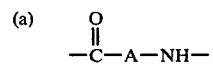

wherein A is $C_1$-$C_{10}$ alkylene or $C_5$-$C_6$ cycloalkylene;

(b) 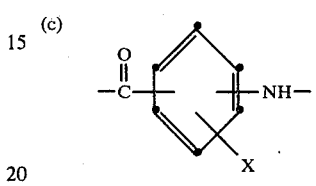

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamoyl, or $C_1$-$C_3$ alkylcarbamoyl;

(c) 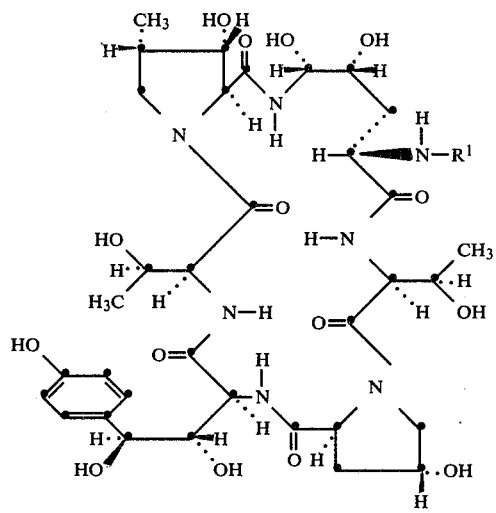

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamoyl, or $C_1$-$C_3$ alkylcarbamoyl;

(d) 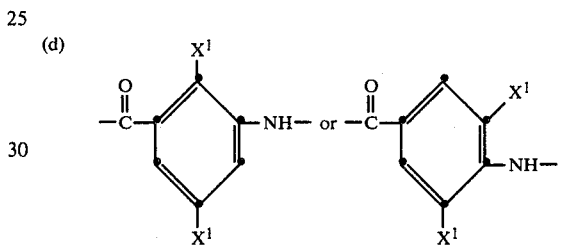

wherein $X^1$ is chloro, bromo, or iodo;

(e) 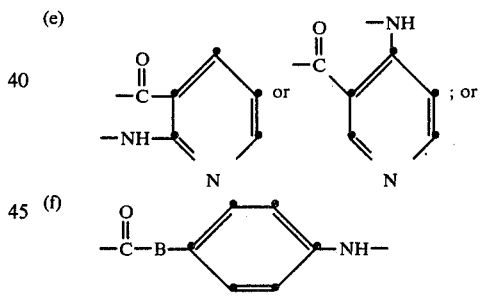; or (f) 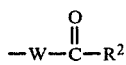

wherein B is a divalent radical of the formula: —$(CH_2)_n$—, wherein n is an integer from 1 to 3; —CH=CH—; —CH=CH—$CH_2$—; or

and $R^2$ is $C_1$-$C_{17}$ alkyl or $C_2$-$C_{17}$ alkenyl.

The terms "alkylene", "alkyl", "alkoxy", "alkylthio", and "alkenyl" refer to both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative, preferred $C_1$-$C_{10}$ alkylene radicals are:
—$CH_2$—;

in which $R^5$ is $C_1$-$C_4$ alkyl (i.e., methyl, ethyl, n-propyl, isopropyl, n-butyl, tert-butyl, isobutyl, or 1-methylpropyl); —$(CH_2)_m$— in which m is an integer from 2 to 10, and

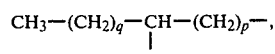

in which p is an integer from 1 to 8 and q is an integer from 0 to 7, provided that n+m must be no greater than 8.

Illustrative, preferred $C_1$-$C_{17}$ alkyl groups are:
(a) $CH_3$—;
(b) —$(CH_2)_nCH_3$ wherein n is an integer from 1 to 16; and
(c)

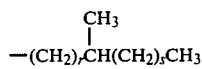

wherein r and s are independently an integer from 0 to 14 provided that r+s can be no greater than 14.

Illustrative, preferred $C_2$-$C_{17}$ alkenyl radicals are:
(a) —$(CH_2)_t$—$CH$=$CH$—$(CH_2)_u$—$CH_3$ wherein t and u are independently an integer from 0 to 14 provided that t+u can be no greater than 14; and
(b) —$(CH_2)_v$—$CH$=$CH$—$(CH_2)_y$—$CH$=$CH$—$(CH_2)_z$—$CH_3$ wherein v and z are independently an integer from 0 to 11 and y is an integer from 1 to 12 provided that v+y+z can be not greater than 11. In particular, the following $C_1$-$C_{17}$ alkyl groups are preferred.

$CH_3$—
$CH_3(CH_2)_5$—
$CH_3(CH_2)_6$—
$CH_3(CH_2)_8$—
$CH_3(CH_2)_{10}$—
$CH_3(CH_2)_{12}$—
$CH_3(CH_2)_{14}$—
$CH_3(CH_2)_{16}$—

The following $C_2$-$C_{17}$ alkenyl groups are especially preferred:

cis-$CH_3(CH_2)_5CH$=$CH(CH_2)_7$—
trans-$CH_3(CH_2)_5CH$=$CH(CH_2)_7$—
cis-$CH_3(CH_2)_{10}CH$=$CH(CH_2)_4$—
trans-$CH_3(CH_2)_{10}CH$=$CH(CH_2)_4$—
cis-$CH_3(CH_2)_7CH$=$CH(CH_2)_7$—
trans-$CH_3(CH_2)_7CH$=$CH(CH_2)_7$—
cis-$CH_3(CH_2)_5CH$=$CH(CH_2)_9$—
trans-$CH_3(CH_2)_5CH$=$CH(CH_2)_9$—
cis,cis-$CH_3(CH_2)_4CH$=$CHCH_2CH$=$CH(CH_2)_7$—
trans,trans-$CH_3(CH_2)_4CH$=$CHCH_2CH$=$CH(CH_2)_7$—
cis,cis,cis-$CH_3CH_2CH$=$CHCH_2CH$=$CHCH_2CH$=$CH$—$(CH_2)_7$—.

When "W" is a divalent radical of the formula

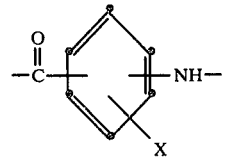

a preferred embodiment is that in which X is hydrogen and the

and —NH— functions are oriented in the para configuration.

The terms "substituted phenyl" and "substituted benzyl", as defined by $R^3$ in formula 4, contemplate substitution of a group at any of the available positions in the benzene ring—i.e. the substituent may be in the ortho, meta, or para configuration.

The term "$C_1$-$C_3$ alkyl", as defined by $R^3$ or X in formula 4, includes the methyl, ethyl, n-propyl, or isopropyl groups.

B. Debono Group II

In the group of derivatives of structure 4 described in Debono application Ser. No. 103,012 (Debono Group II), $R^1$ is a substituted benzoyl group of the formula 5:

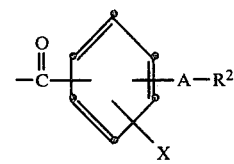

wherein A is divalent oxygen, sulfur, sulfinyl, or sulfonyl; X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamoyl, or $C_1$-$C_3$ alkylcarbamoyl; and $R^2$ is $C_5$-$C_{18}$ alkyl or $C_5$-$C_{18}$ alkenyl.

In the substituted benzoyl group ($R^1$), the

function and the —$AR^2$ function may be oriented on the benzene ring in the ortho, meta, or para position relative to each other. The para orientation is preferred. The substituent represented by X may be substituted at any available position of the benzene ring not occupied by the

and $AR^2$ groups.

The terms "alkyl" and "alkenyl" are as defined in the Group I derivatives.

Illustrative, preferred $C_5$-$C_{18}$ alkyl radicals are:
(a) —$(CH_2)_nCH_3$ wherein n is an integer from 4 to 17; and (b)

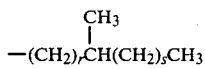

wherein r and s are, independently, an integer from 0 to 15, provided that r+s can be no greater than 15 or no less than 2.

Illustrative, preferred $C_5$-$C_{18}$ alkenyl radicals are:

(a) —$(CH_2)_t$—CH=CH—$(CH_2)_n$—$CH_3$ wherein t is an integer from 1 to 15, and n is an integer from 0 to 15 provided that t+n can be no greater than 15 or no less than 2; and (b) —$(CH_2)_v$—CH=CH—$(CH_2)_y$—CH=CH—$(CH_2)_z$—$CH_3$ wherein v and z are, independently, an integer from 0 to 12 and y is an integer from 1 to 13 provided that v+y+z must be no greater than 13.

Preparation of the Derivatives

The compounds of formulas 3 and 4 are prepared by acylating A-30912A nucleus at the α-amino group of the dihydroxyornithine portion of the nucleus with the appropriate acyl side chain using methods conventional in the art for forming an amide bond. The acylation is accomplished, in general, by reacting A-30912A nucleus with an activated derivative of the acid corresponding to the desired acyl side chain group.

The term "activated derivative" means a derivative which renders the carboxyl function of the acylating agent reactive to coupling with the primary amino group to form the amide bond which links the acyl side chain to the A-30912A nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride or aryloxyformic acid anhydride) or (c) an activated ester (e.g. a 2,4,5-trichlorophenyl ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of formulas 3 and 4 is by the active ester method. The use of the 2,4,5-trichlorophenyl ester of the desired acid as the acylating agent is most preferred. In this method, an excess amount of the active ester is reacted with A-30912A nucleus at room temperature in a non-reactive organic solvent such as dimethylformamide (DMF). The reaction time is not critical, although a time of about 15 to about 18 hours is preferred. At the conclusion of the reaction, the solvent is removed, and the residue is purified by a recognized method, such as by column chromatography. Chromatography using silica gel as the stationary phase and ethyl acetate:methanol (3:2) as the solvent system is a preferred method.

The 2,4,5-trichlorophenyl esters of the corresponding acids can be prepared conveniently by treating the desired acid with 2,4,5-trichlorophenol in the presence of a coupling agent, such as N,N'-dicyclohexylcarbodiimide. Other methods suitable for preparing acid esters will be apparent to those skilled in the art.

The alkanoic and alkenoic acids used as starting materials for the Abbott and Fukuda derivatives of formula 3 and the activated derivatives thereof (in particular, the acid chlorides and the 2,4,5-trichlorophenyl esters), are known compounds and can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide. The 2,4,5-trichlorophenyl ester derivative can be purified by column chromatography over silica gel in toluene.

The N-alkanoylamino acids or N-alkenoylamino acids used as starting materials for the Debono Group I derivatives of formula 4 are either known compounds or they can be made by acylating the appropriate amino acid with the appropriate alkanoyl or alkenoyl group using conventional methods. A preferred way of preparing the N-alkanoylamino acids is by treating the appropriate amino acid with an alkanoic acid chloride in pyridine. The alkanoic acids, the activated derivatives thereof, and the amino acids used are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent used to attach the N-alkanoyl or N-alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids used in the synthesis of these products may exist in optically active forms. Both the natural configuration (L-configuration) and unnatural configuration (D-configuration) may be used as starting materials.

The substituted benzoic acids used as starting materials for the Debono II derivatives and the activated derivatives thereof are either known compounds or they can be made from known compounds by methods known in the art. The alkoxybenzoic acids or alkenyloxybenzoic acids can be prepared conveniently from an appropriate hydroxybenzoic acid by reacting an appropriate alkyl or alkenyl halide with the disodium salt of the appropriate hydroxybenzoic acid. The (alkylthio)benzoic acids or the (alkenylthio)benzoic acids can be prepared conveniently by treating the appropriate substituted S-(4-carbomethoxyphenyl)dimethylthiocarbamate of the general formula $CH_3CO_2C_6H_3X$-$S(CO)N(CH_3)_2$ with aqueous sodium hydroxide at 65°–85° C., then adding the appropriate alkyl or alkenyl bromide, and continuing heating for 2–4 hours. The substituted S-(4-carbomethoxyphenyl)dimethylthiocarbamates can be made from the appropriate hydroxybenzoic acids by the method of M. Newman and H. Kanes, *J. Org. Chem.* 31, 3980 (1966).

When it is desired to prepare a Debono II derivative of formula 4 wherein A is sulfinyl or sulfonyl, the appropriate sulfoxide or sulfone derivative of the (alkenylthio)- or (alkylthio)benzoic acid (formula 5) can be used for acylation of the nucleus. The appropriate sulfoxides or sulfones can be made by oxidation of the corresponding thioether compound using conventional agents, such as m-chloroperbenzoic acid, tert-butyl hypochlorite, sodium metaperiodate, or hydrogen peroxide. If a double bond is present in the thioether, very mild conditions should be used to avoid epoxidation. If equimolar amounts of reactants are taken, the product is a sulfoxide (A is sulfinyl), which is readily oxidized to the sulfone (A is sulfonyl) by an additional mole of the oxidizing agent.

The hydroxybenzoic acids and substituted derivatives thereof used as starting materials in the processes described herein are either known compounds or can be prepared by conventional methods which are known in the art.

Utility of the Derivatives

The derivatives of the A-30912A nucleus, i.e. the compounds of formulas 3 and 4, inhibit the growth of pathogenic fungi as evidenced by standard biological test procedures. The compounds are useful, therefore, for controlling the growth of fungi on environmental surfaces (as an antiseptic) or in treating infections caused by fungi. The antifungal activity of the compounds has been demonstrated against *Candida albicans* in vitro in agar-plate disc-diffusion tests and in agar tube-dilution tests, and in vivo in tests in mice infected with *C. albicans*. Thus, the compounds are particularly useful in treating infections caused by strains of *C. albicans* (candidosis). The compounds of formulas 3 and 4 have also shown activity in vitro in agar-plate disc-diffusion tests against *Trichophyton mentagrophytes*, a dermatophytic organism. Activity has also been found in in vitro agar-plate disc-diffusion tests against *Saccharomyces pastorianus* and *Neurospora crassa*. Certain compounds (as shown in Example 13, Table VIII) give significant blood levels upon oral administration in mice.

When given to a dog by intravenous administration at a dosage level of 100 mg/kg per day for five days, the compound of formula 4 wherein $R^1$ is p-(n-octyloxy)benzoyl showed no outward signs of toxicity, although temporarily increased SGPT levels were observed.

When used systemically, the dosage of the compounds of formulas 3 and 4 will vary according to the particular compound being used, the severity and nature of the infection, and the physical condition of the subject being treated. Therapy should be initiated at low dosages, and the dosage should be increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose, may be added to make the solutions isotonic. The proportions and nature of such additives will be apparent to those skilled in the art.

Certain compounds of formulas 3 and 4 give significant blood levels after oral administration (see Example 13, Table VIII) and can be administered systemically by the oral route. For oral use, such compounds can be administered in combination with pharmaceutically acceptable carriers or excipients in the form of capsules, tablets or powders. The nature and proportion of such carriers or excipients will be recognized by those skilled in the art.

When used to treat vaginal Candida infections, the compounds of formulas 3 and 4 can be administered in combination with pharmaceutically acceptable conventional excipients suitable for intravaginal use. Formulations adapted for intravaginal administration will be known to those skilled in the art.

In order to illustrate the operation of this invention more fully, the following examples are provided.

EXAMPLE 1

Preparation of A-30912A Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

MEDIUM A

| Ingredient | Amount |
|---|---|
| Baby oatmeal | 60.0 g |
| Yeast | 2.5 g |
| $K_2HPO_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.

*Czapek's mineral stock has the following composition:

| Ingredient | Amount |
|---|---|
| $FeSO_4 \cdot 7H_2O$ (dissolved in 2 ml conc HCl) | 2 g |
| KCl | 100 g |
| $MgSO_4 \cdot 7H_2O$ | 100 g |
| Deionized water | q.s. to 1 liter |

MEDIUM B

| Ingredient | Amount |
|---|---|
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| $MgSO_4 \cdot 7H_2O$ | 0.25 g |
| $CaCO_3$ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| $K_2HPO_4$ | 1.0 g |
| Czapek's mineral stock | 5.0 ml |
| Deionized water | q.s. to 1 liter | adjust to pH 7.4 with NaOH; after autoclaving, pH is

| Ingredient | Amount |
|---|---|
| about 6.8. | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen," *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

MEDIUM I

| Ingredient | Amount (g/L) |
|---|---|
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4 \cdot 7H_2O$ | 0.25 |
| Tap water | q.s. to 1 liter |

The pH of the medium is about 6.9 after sterilization by autoclaving at 121° C. for 45 minutes at about 16–18 psi.

MEDIUM II

| Ingredient | Amount (g/L) |
|---|---|
| Sucrose | 30.0 |
| Peptone | 5.0 |
| $K_2HPO_4$ | 1.0 |
| KCl | 0.5 |
| $MgSO_4 \cdot 7H_2O$ | 0.5 |
| $FeSO_4 \cdot 7H_2O$ | 0.002 |
| Deionized water | q.s. to 1 liter |
| Adjust to pH 7.0 with HCl; after autoclaving, pH is about 7.0. | |

MEDIUM III

| Ingredient | Amount (g/L) |
|---|---|
| Glucose | 20.0 |
| $NH_4Cl$ | 3.0 |
| $Na_2SO_4$ | 2.0 |
| $ZnCl_2$ | 0.019 |
| $MgCl_2 \cdot 6H_2O$ | 0.304 |
| $FeCl_3 \cdot 6H_2O$ | 0.062 |
| $MnCl_2 \cdot 4H_2O$ | 0.035 |
| $CuCl_2 \cdot 2H_2O$ | 0.005 |
| $CaCO_3$ | 6.0 |
| $KH_2PO_4$* | 0.67 |
| Tap water | q.s. to 1 liter |

*Sterilized separately and added aseptically Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of A-30912 Factor A

A fermentation of *A. utahensis* is carried out as described in Sect. A, using slant medium A and production medium I and incubating the production medium for about 42 hours. A-30912 factor A (340 g. of crude substrate which contained about 19.7 g. of A-30912 factor A, dissolved in 1.5 L ethanol) is added to the fermentation medium.

Deacylation of A-30912 factor A is monitored by assay against *Candida albicans*. The fermentation is allowed to continue until deacylation is complete as indicated by disappearance of activity vs. *C. albicans*.

C. Isolation of A-30912A Nucleus

Whole fermentation broth (100 liters), obtained as described in Sect. B and containing nucleus from about 20 g of A-30912 factor A, is filtered. The mycelial cake is discarded. The clear filtrate thus obtained (about 93 liters) is passed through a column containing 4.5 liters of HP-20 resin (DIAION High Porous Polymer, HP-Series, Mitsubishi Chemical Industries Limited, Tokyo, Japan) at a rate of 200 ml/minute. The effluent thus obtained is discarded. The column is then washed with up to eight column volumes of deionized water at pH 6.5–7.5 to remove residual filtered broth. This wash water is discarded. The column is then eluted with a water:methanol (7:3) solution (85 liters) at a rate of 200–300 ml/minute.

Elution is monitored using the following procedure: Two aliquots are taken from each eluted fraction. One of the aliquots is concentrated to a small volume and is treated with an acid chloride such as myristoyl chloride, using a procedure such as that described in Example 10. This product and the other (untreated) aliquot are assayed for activity against *Candida albicans*. If the untreated aliquot does not have activity and the acylated aliquot does have activity, the fraction contains A-30912A nucleus. The eluate containing the A-30912A nucleus is concentrated under vacuum to a small volume and lyophilized to give approximately 97 grams of crude nucleus.

D. Purification of A-30912A Nucleus by Reversed-Phase Liquid Chromatography

Crude A-30912A nucleus (25 grams), obtained as described in Section C, is dissolved in 300 ml of water- :acetonitrile:acetic acid:pyridine (96:2:1:1). This solution is chromatographed on a 4-liter stainless-steel column (8 cm × 80 cm) filled with Lichroprep RP-18, particle size 25-40 microns (MC/B Manufacturing Chemists, Inc. E/M, Cincinnati, Ohio). The column is part of a Chromatospac Prep 100 unit (Jobin Yvon, 16-18 Rue du Canal 91160 Longjumeau, France). The column is operated at a pressure of 90-100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Nebr. 68504) with an optical unit (ISCO Type 6). Fractions having a volume of about 500 ml are collected each minute.

On the basis of absorption at 280 nm, fractions containing A-30912A nucleus are combined, evaporated under vacuum and lyophilized to give 2.6 grams of nucleus. The amount of solvent required to complete this chromatographic separation process varies from 7-8 liters.

EXAMPLE 2

A-30912A nucleus is prepared and purified by the method of Example 1 except that tetrahydro-A-30912A is used as the substrate.

EXAMPLE 3

A-30912A nucleus is prepared and purified by the method of Example 1 except that aculeacin A is used as the substrate.

EXAMPLE 4

Preparation of the A-42355 Antibiotic complex

A. Shake-Flask Fermentation

A culture of *Aspergillus nidulans* var. *roseus* NRRL 11440 is prepared and maintained on an agar slant prepared with medium having the following composition:

| Ingredient | Amount |
| --- | --- |
| Glucose | 5 g |
| Yeast extract | 2 g |
| CaCO$_3$ | 3 g |
| Vegetable juice* | 200 ml |
| Agar** | 20 g |
| Deionized water | q.s to 1 liter |
| (initial pH 6.1) | |

*V-8 Juice, Campbell Soup Co., Camden, N.J.
**Meer Corp.

The slant is inoculated with *Aspergillus nidulans* var. *roseus* NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount | |
| --- | --- | --- |
| Sucrose | 25 | g |
| Blackstrap molasses | 36 | g |
| Corn-steep liquor | 6 | g |
| Malt extract | 10 | g |
| K$_2$HPO$_4$ | 2 | g |
| Enzymatic hydrolysate of casein* | 10 | g |
| Tap Water | 1100 | ml |

-continued

| Ingredient | Amount |
| --- | --- |
| (initial pH 6.5-6.7) | |

*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows:

The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

MEDIUM IV

| Ingredient | Amount | |
| --- | --- | --- |
| ZnSO$_4$ . 7H$_2$O | 0.00455 | g/L |
| Soluble meat peptone* | 30.5 | g/L |
| Soybean meal | 15.5 | g/L |
| Tapioca dextrin** | 2.0 | g/L |
| Blackstrap molasses | 10.5 | g/L |
| Enzymatic hydrolysate of casein*** | 8.5 | g/L |
| Na$_2$HPO$_4$ | 4.5 | g/L |
| MgSO$_4$ . 7H$_2$O | 5.5 | g/L |
| FeSO$_4$ . 7H$_2$O | 0.1 | g/L |
| Cottonseed oil | 40.0 | ml |
| (Antifoam)**** | 1.0 | ml |
| Tap Water | 1000.0 | ml |

MEDIUM IV-continued

| Ingredient | Amount |
| --- | --- |
| (initial pH 6.8–7.0) | |

*O.M. Peptone, Amber Laboratories, Juneau, Wisc.
**Stadex 11, A.E. Staley Co., Decatur, Ill.
***N-Z-Amine A, Humko Sheffield Chemical, Lyndhurst, N.J.
****P2000, Dow Corning, Midland, Michigan

MEDIUM V

| Ingredient | Amount |
| --- | --- |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap Water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount | |
| --- | --- | --- |
| Sucrose | 25 | g |
| Blackstrap molasses | 25 | g |
| Corn-steep liquor | 6 | g |
| Enzymatic hydrolysate of casein* | 10 | g |
| Malt extract | 10 | g |
| $K_2HPO_4$ | 2 | g |
| Tap Water | 1000 | ml |
| (initial pH 6.1) | | |

*N-Z-Case

EXAMPLE 5

Separation of the A-42355 Antibiotic Complex

Whole fermentation broth (4127 liters), obtained by the method described in Example 4 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 6

Isolation of A-30912 Factor A

A-42355 antibiotic complex (1 g), prepared as described in Example 5, is dissolved in 7 ml of methanol:water:acetonitrile (7:2:1). This solution is filtered and introduced onto a 3.7-cm I.D.×35-cm glass column [Michel-Miller High Performance Low Pressure (HPLPLC) Chromatography Column, Ace Glass Incorporated, Vineland, N.J. 08360] packed with LP-1/$C_{18}$ silica gel reversed-phase resin (10–20 microns), prepared as described in Example 7, through a loop with the aid of a valve system. The column is packed in methanol:water:acetonitrile (7:2:1) by the slurry-packing procedure described in Example 8. An F.M.I. pump with valveless piston design (maximum flow 19.5 ml/minute) is used to move the solvent through the column at a flow rate of 9 ml/minute at ca. 100 psi, collecting fractions every minute. Elution of the antibiotic is monitored at 280 nm by using a UV monitor (ISCO Model UA-5, Instrument Specialist Co., 4700 Superior Ave., Lincoln, Nebr. 68504) with an optical unit (ISCO Type 6).

Fractions (about 112–140) are combined and added to 20 ml of water. The pH of this solution is adjusted to pH 4.0 with N HCl. The resulting solution is extracted twice with equal volumes of chloroform. The two chloroform extracts are combined and concentrated under vacuum to give an oil. The oil is dissolved in tertiary butanol, and this solution is lyophilized to give 524 mg of A-42355 factor A (A-30912 factor A; A-22082).

EXAMPLE 7

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 8

Slurry Packing Procedure for Michel-Miller Columns

General Information

A. Analytical or preparative columns can be packed by this procedure.

B. Silica gels and silica gel reversed phase packings (e.g., Quantum LP-1, particle size 10–20 microns; Li-Chroprep RP-8 and RP-18, particle size 24–40 microns) are recommended. However, other silica gels (e.g., Shandons ODS Hypersil, particle size 5 microns) as well as other types of resins have been packed successfully by this procedure.

C. Generally, a pressure of less than 200 psi and flow rates between 5–40 ml/minute are required for this slurry packing technique; this is dependent on column volume and size. PLEASE NOTE: Packing pressure should exceed pressure used during actual separation by 30–50 psi; this will assure no further compression of the adsorbent during separation runs. Columns packed by this procedure with reversed-phase silica gel can be operated for several years without loss of efficiency.

D. Sudden decrease in pressure may cause cracks or channels to form in the packing material, which would greatly reduce column efficiency. Therefore, it is important to let the pressure drop slowly to zero whenever the pump has been turned off.

E. Approximate volume of columns (Ace Glass Cat. No., unpacked): 5795-04, 12 ml; 5795-10, 110 ml; 5795-16, 300 ml; 5795-24, 635 ml; and 5796-34, 34 ml.

F. The time required to pack a glass column will vary from minutes to several hours depending on column size and experience of the scientist.

Example

1. Connect glass column to a reservoir column via coupling (volume of reservoir column should be twice that of the column). Place both columns in vertical positions (reservoir column above).

2. Weigh out packing material (ca. 100 g for 200 ml colunn).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. NOTE: The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure.

NOTE: Always allow pressure to decrease slowly after turning off pump—this will prevent formation of any cracks or channels in the packing material.

10. Relieve pressure and disconnect pre-column carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 9

Preparation of Tetrahydro-A-30912A

A-30912 factor A is dissolved in ethanol. $PtO_2$ in absolute ethanol is reduced to form Pt, which in turn is used to reduce the A-30912 factor A catalytically, using hydrogenation under positive pressure until the reaction is complete (about 2–3 hours). The reaction mixture is filtered and concentrated under vacuum. The residue is dissolved in a small amount of tert-butanol and lyophilized to give tetrahydro-A-30912A.

EXAMPLE 10

Preparation of an Abbott and Fukuda Derivative

The following procedure illustrates the preparation of the compounds of formula 3 by the "active ester" method. The specific compound prepared by this procedure is the compound of formula 3 wherein $R^1$ is $CH_3(CH_2)_{11}$—(n-dodecyl).

n-Tridecanoyl Derivative of A-30912A Nucleus

A. Preparation of 2,4,5-Trichlorophenyl Tridecanoate

A solution of n-tridecanoic acid (Sigma Chemical Co, 12.5 g), 2,4,5-trichlorophenol (11.5 g), and N,N'-dicyclohexylcarbodiimide (12.0 g) in methylene chloride (650 ml) is stirred at room temperature for 16 hours. The reaction mixture is then filtered and dried in vacuo to give 2,4,5-trichlorophenyl tridecanoate (22 g). The material is purified by column chromatography over silica gel (Woelm) using toluene as the eluent. Fractions are monitored by TLC using a shortwave UV light for detection. Fractions containing the purified product are pooled and concentrated in vacuo to dryness.

B. Acylation of A-30912 Nucleus with 2,4,5-Trichlorophenyl Tridecanoate

A solution of 2,4,5-trichlorophenyl tridecanoate (6.0 g) and A-30912A nucleus (4.5 g) in dimethylformamide (DMF) (600 ml) is stirred at room temperature for 16 hours. Removal of solvent in vacuo affords a residue (12 g). The residue is slurried with methylene chloride (500 ml) for 45 minutes, and the mixture is filtered. The filtrate is discarded. The remaining solids are extracted with methanol (500 ml). The methanol extract is filtered and concentrated in vacuo to give a crude product (5.0 g).

The crude product is purified by reversed phase HPLC as follows:

A sample of the crude product (1 g), dissolved in methanol (5 ml), is injected into a 1-×32-in stainless steel column packed with LP-1/$C_{18}$ resin (see Examples 7 and 8). The column is eluted with a solvent system comprising $H_2O:CH_3OH:CH_3CN$ (3:3:4). The elution is performed at a pressure of 1000–1500 psi with a flow rate of 11–12 ml/min using an LDC duplex pump (Milton-Roy). The effluent is monitored by an ultraviolet detector (ISCO-UA-5) at 280 nm. Fractions are collected every two minutes (21–24 ml). The fractions containing the desired product are pooled and dried in vacuo. Yield of the product: 550 mg. The above-described chromatography is repeated four times to give additional purified samples of the product as follows: 620 mg, 520 mg, 670 mg, and 490 mg to give a total weight of 2.8 g.

Following the above procedure 40 g of A-30912A nucleus is reacted with 2,4,5-trichlorophenyl n-tridecanoate to give 2.6 g of purified title product. The materials from both preparations (5.4 g) are combined. Mass ion by FDMS ($M^+ + Na^+$): 1016. (Theoretical: $M^+ + Na^+ = 1016$). Analytical HPLC ($C_{18}$ Micro Bondapak, Waters Co.) with eluent system $H_2O:CH_3OH:CH_3CN$ (2:1:2) shows only one peak.

EXAMPLE 11

Preparation of a Debono Group I Derivative

The following procedure illustrates the preparation of the Debono Group I compounds of formula 4. The specific compound prepared by this procedure is the compound of Formula 4 wherein $R^1$ is N-(n-dodecanoyl)-p-aminobenzoyl.

Preparation of N-(n-Dodecanoyl)-p-aminobenzoyl Derivative of A-30912 Nucleus

A. Preparation of N-(n-Dodecanoyl)-p-aminobenzoic Acid n-Dodecanoyl chloride (8.74 g; 40 mmoles) is added dropwise to a solution of p-aminobenzoic acid (5.5 g; 40 mmoles) dissolved in pyridine (100 ml). The mixture is stirred for 3 hours and poured into water (3 L). The precipitate which forms is filtered and dried in vacuo to give N-(n-dodecanoyl)-p-aminobenzoic acid (11.01 g).

B. Preparation of the 2,4,5-Trichlorophenyl Ester of N-(n-Dodecanoyl)-p-aminobenzoic Acid N-(n-Dodecanoyl)-p-aminobenzoic acid (11.01 g; 34.5 mmoles), 2,4,5-trichlorophenol (7.5 g; 38 mmoles), and N,N'-dicyclohexylcarbodiimide (6.94 g; 34.5 mmoles) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g).

C. Acylation of A-30912A Nucleus

A-30912A nucleus (8.16 g; 10.2 mmoles) and the 2,4,5-trichlorophenyl ester of N-(n-dodecanoyl)-p-aminobenzoic acid (4.72 g; 10.2 mmoles) are dissolved in dimethylformamide (100 ml). The solution is stirred at room temperature for 15 hours. Solvent is removed in vacuo to give a residue which is washed twice with diethyl ether. The washes are discarded. The washed residue is dissolved in methanol (50 ml) and is purified by reversed phase HPLC by means of a "Prep LC/System 500" unit (Waters Associates, Inc., Milford, Mass.) using a Prep Pak-500/$C_{18}$ column (Waters Associates, Inc.,) as the stationary phase. The column is eluted isocratically with $H_2O:CH_3OH:CH_3CN$ (25:65:10 v/v) at 500 psi. The fractions are analyzed by TLC using silica gel plates and $H_2O:CH_3OH:CH_3CN$ (25:65:10 v/v) as the solvent system. Fractions containing the desired product are combined and lyophilized to give the N-(n-dodecanoyl)-p-aminobenzoyl derivative of A-30912A nucleus (3.5 g).

EXAMPLE 12

Preparation of a Debono Group II Derivative

The following procedure illustrates the preparation of the Debono Group II compounds of formula 4. The specific compound prepared by this procedure is the compound of formula 4 wherein $R^1$ is p-(n-octyloxy)-benzoyl.

Preparation of the p-(n-Octyloxy)benzoyl Derivative of A-30912A Nucleus

A. Preparation of p-(n-Octyloxy)benzoic Acid

A solution of p-hydroxybenzoic acid (19.2 g, 150 mmoles) in 10% aqueous sodium hydroxide (120 ml) is added to dimethyl sulfoxide (DMSO) (480 ml) previously heated to 80° C. n-Octyl bromide (28.95 g, 150 mmoles) is added dropwise to the solution. The reaction mixture is stirred for 4 hours at room temperature after which it is poured into ice water (1200 ml). Conc. hydrochloric acid (30 ml) is added, and the mixture is allowed to stand until precipitation is complete. The precipitate is collected, dried, and crystallized from acetonitrile-water. mp 97°–99° C.

Analysis for $C_{15}H_{22}O_3$: Calculated: C, 71.97; H, 8.86. Found: C, 71.72; H, 9.10.

B. Preparation of the 2,4,5-Trichlorophenyl Ester of p-(n-Octyloxy)benzoic Acid p-(n-Octyloxy)benzoic acid (6.18 g, 24.7 mmoles), 2,4,5-trichlorophenol (5.39 g, 27.2 mmoles), and N,N'-dicyclohexylcarbodiimide (4.94 g, 24.7 mmoles) are dissolved in methylene chloride (200 ml). The mixture is stirred at room temperature for 18 hours and then is filtered. The filtrate is evaporated to give an oil, which is crystallized from $CH_3CN:H_2O$ to give the 2,4,5-trichlorophenyl ester of p-(n-octyloxy)benzoic acid.

NMR Analysis: $\delta 4.02$ (2H, t, J=3 Hz), $\delta 7.0$ (1H, d, J=4 Hz), 7.23 (s, 1H), 7.3 (s, 1H), 8.08 (d, 1H, J=4 Hz).

C. Acylation of A-30912A Nucleus

A-30912A nucleus (14.2 g, 17.8 mmoles) and the 2,4,5-trichlorophenyl ester of p-(n-octyloxy)benzoic acid (15.32 g, 35.7 mmoles) are dissolved in dimethylformamide (150 ml). The solution is stirred at room temperature for 16–20 hours. Solvent is removed in vacuo, and the residue is washed twice with diethyl ether and twice with methylene chloride. The washes are discarded. The washed residue is dissolved in ethylacetate:methanol (1:3, 80 ml) and is purified by HPLC using a "Prep LC/System 500" unit with silica gel as the stationary phase. The column is eluted stepwise with methanol:ethyl acetate (1:4 to 2:3) solvent systems. The fractions are analyzed by silica gel (Merck) TLC using an ethyl acetate:methanol (3:2 v/v)

as the solvent system. Fractions devoid of A-30912A nucleus are pooled and lyophilized to give the p-(n-octyloxy)benzoyl derivative of A-30912A nucleus. Yield: 7.13 g; M+ +23: 1052 (by FDMS).

EXAMPLE 13

The antifungal activity of the compounds of formulas 3 and 4 can be demonstrated in vitro in standard disc-diffusion tests and agar-dilution tests and in vivo in standard tests in mice which assess effectiveness against a systemic fungal infection. The results of the antifungal testing of representative compounds of formulas 3 and 4 are set forth in Tables IV through VIII.

Tables IV and V give the results of the testing in vitro of the compounds of Examples 10–12 by agar-plate disc-diffusion methods. In Table IV activity is measured by the size (diameter in mm) of the observed zone of inhibition of the microorganism produced by the test compound. In Table V activity is measured by the minimal inhibitory concentration (MIC) of the substance (mg/disc) required to inhibit growth of the test organism. Table VI gives the results of the testing in vitro of the p-(n-octyloxy)benzoyl derivative of A-30912A nucleus (Formula 4, $R^1$ is p-(n-octyloxy)benzoyl) against five strains of *Candida albicans* by the agar-dilution method. In Table VI activity is measured by the minimal inhibitory concentration (MIC) of the substance (mg/ml) required to inhibit the test organism.

The results of in vivo tests to evaluate the effectiveness of the derivatives against an infection caused by *Candida albicans* A-26 in mice are given in Table VII. In these tests activity is measured by the $ED_{50}$ value (the dose in mg/kg required to cure 50% of the test animals). Where an $ED_{50}$ value was not obtained, activity is indicated by the lowest dose at which a significant antifungal effect is observed. In these tests, groups of male albino mice (specific pathogen free), weighing 18 to 20 grams, are infected intraveneously with *Candida albicans* A-26. The animals are X-irradiated 24 hours prior to infection at about 50 roentgens per minute for 8 minutes (400 total dose) to reduce immune responses to the infecting organism. At 0, 4, and 24 hours post infection each group of mice is given graded doses subcutaneously of the test compound as a suspension in 33% polyethylene glycol(PEG)-water. The day of death for each animal is recorded. Student's t test statistical comparison of the average day of death is made between each group of infected-treated animals at a particular dosage level and 10 infected-untreated animals to determine if treatment significantly extends survival time.

Table VIII gives the results of the testing of the compounds of Examples 10-12 for absorption after oral administration. In these tests, mice are gavaged with a dose of 416 mg/kg of the test compound suspended in 33% PEG 400-water. At time intervals, blood samples are taken from the orbital sinus and are assayed for antibiotic activity as follows: A 7-mm disc containing 20 ml of whole blood is placed on agar seeded with *Aspergillus montevidensis* A35137. After 40 hours incubation at 30° C., zones of inhibition from the blood samples are compared to a standard obtained from the test compound, and the amount of compound in the blood sample is calculated.

TABLE IV

| Antifungal Activity by the Agar-Plate Disc-Diffusion Test | | | | | | |
|---|---|---|---|---|---|---|
| Compound | | | Size of Zone of Inhibition (mm)[a] | | | |
| Example No. | Formula No. | $R^1 =$ | *Saccharomyces pastorianus* X-52 | *Neurospora crassa* 846 | *Trichophyton mentagrophytes* A-23 | *Candida albicans* A-26 |
| 10 | 3 | $CH_3(CH_2)_{11}$— | 21 | 32 | 60* | 30 |
| 11 | 4 | | 21 | 33* | 55* | 23 |
| | | $CH_3(CH_2)_{10}CONH$—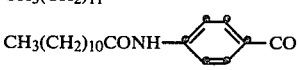—CO— | 17 | 35* | 56* | 19 |
| 12 | 4 | | 18 | 23* | — | 28 |
| | | $CH_3(CH_2)_7O$—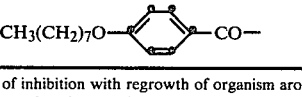—CO— | | | | |

*Distinct measurable zone of inhibition with regrowth of organism around disc.
[a]Compounds were tested as methanol suspensions at a concentration of 1 mg/ml by dipping a 7-mm disc into the suspension and placing it on the agar surface. Incubation: 24–28 hours at 25–37° C.

TABLE V

| Antifungal Activity by the Agar-plate Disc-Diffusion Test | | | | |
|---|---|---|---|---|
| Compound | | | MIC (mg/disc)* | |
| Example No. | Formula No. | $R^1 =$ | *Candida albicans* A-26 | *Trichophyton mentagrophytes* #6 |
| 10 | 3 | $CH_3(CH_2)_{11}$— | 0.625 | 0.039 |
| 11 | 4 | | 0.625 | >0.039 |
| | | $CH_3(CH_2)_{10}CONH$—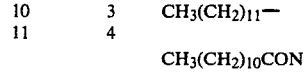—CO— | 1.25 | 0.678 |
| 12 | 4 | | 0.156 | |
| | | $CH_3(CH_2)_7O$—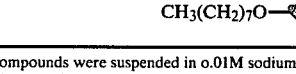—CO— | >0.302(0.312)** | |

*Compounds were suspended in o.01M sodium borate solution, pH 7.5. The compounds were tested at 20 mg/disc at top level and at two-fold dilutions until end points were reached. Incubation: 24 hours; 30° C.
**Against 5 isolates

TABLE VI

In vitro Activity of p-(n-Octyloxy)benzoyl Derivative of A-30912A Nucleus against *Candida albicans* Strains

| MIC (mg/ml) | | | | |
|---|---|---|---|---|
| A26 | SBH 16 | SBH 31 | SBH 28 | SBH 29 |
| 0.312 | 0.312 | 0.312 | 0.312 | 0.312 |

TABLE VII

Therapeutic Activity Against *C. albicans* in Mice

| Example No. | Formula No. | Compound $R^1 =$ | Dosage Schedule* | $ED_{50}$(mg/kg) | Lowest Active Dose (mg/kg) |
|---|---|---|---|---|---|
| 10 | 3 | $CH_3(CH_2)_{11}-$ | B | 34 | 20 |
| 11 | 4 | $CH_3(CH_2)_{10}CONH-\!\!\left<\!\!\bigcirc\!\!\right>\!\!-CO-$ | A | 15 / 15 | 10 / ≧5 |
| 12 | 4 | $CH_3(CH_2)_7O-\!\!\left<\!\!\bigcirc\!\!\right>\!\!-CO-$ | A | 13 / 22.2 | 10 / >12.5 |

*Dosage Schedules: A = 40, 20, 15, and 10 mg/kg; B = 80, 40, 20 and 10 mg/kg. Dosage given 0, 4, and 24 hours post injection as suspension of test compound in 30% PEG—H₂O. Number of mice receiving test compounds at each dosage level: 6 mice per group. Number of mice in control (untreated) group: 10 mice per group.
**As measured by increase in survival time of treated animals versus control, calculated by method of L. J. Reed and H. Muench, Amer. J. Hygiene, 27, 493–497 (1938).

TABLE VIII

Blood Levels After Oral Administration in Mice

| Example No. | Formula No. | Compound $R^1 =$ | Blood Levels* (mg/ml) |
|---|---|---|---|
| 10 | 3 | $CH_3(CH_2)_{11}-$ | 0.10 |
| 11 | 4 | $CH_3(CH_2)_{10}CONH-\!\!\left<\!\!\bigcirc\!\!\right>\!\!-CO-$ | 0.83 |
| 12 | 4 | $CH_3(CH_2)_7O-\!\!\left<\!\!\bigcirc\!\!\right>\!\!-CO-$ | 23. |

*Four hours after administration of test compound at dose of 416 mg/kg by gavage as suspension of compound in 33% PEG 400-H₂O. Compound determined by bioassay vs. *Aspergillus montevidensis* A-35137.

We claim:

1. A-30912A nucleus of the formula

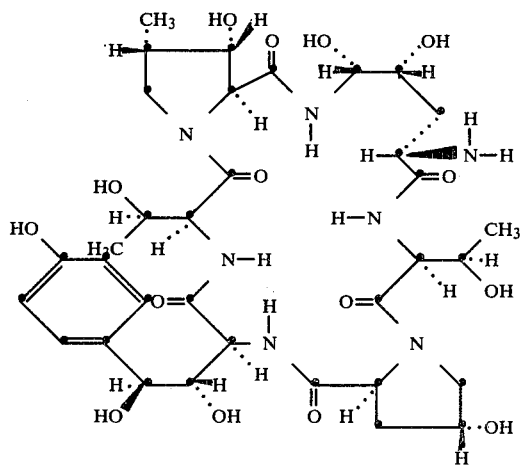

and the acid addition salts thereof.

2. The compound of claim 1 which is A-30912A nucleus.

3. The method of deacylating an antibiotic selected from the group consisting of A-30912 factor A, tetrahydro A-30912A, and aculeacin A which comprises exposing the antibiotic in an aqueous medium to an enzyme which deacylates and which is produced by a microorganism of the family Actinoplanaceae until substantial deacylation is accomplished.

4. The method of claim 3 wherein the microorganism of the family Actinoplanaceae is a member of the genus Actinoplanes.

5. The method of claim 4 wherein the microorganism is *Actinoplanes utahensis*.

6. The method of claim 5 wherein the microorganism is *A. utahensis* NRRL 12052 or a mutant thereof which produces the enzyme.

7. The method of claim 6 wherein the microorganism is *A. utahensis* NRRL 12052.

8. The method of claim 3 wherein the microorganism is *Streptosporangium roseum* var. *hollandensis* NRRL 12064, or a mutant thereof which produces the enzyme.

9. The method of claim 8 wherein the microorganism is *Streptosporangium roseum* var. *hollandensis* NRRL 12064.

10. The method of claim 4 wherein the microorganism is *Actinoplanes missouriensis* NRRL 12053 or a mutant thereof which produces the enzyme.

11. The method of claim 10 wherein the microorganism is *Actinoplanes missouriensis* NRRL 12053.

12. The method of claim 4 wherein the microorganism is Actinoplanes sp. NRRL 12065 or a mutant thereof which produces the enzyme.

13. The method of claim 12 wherein the microorganism is Actinoplanes sp. NRRL 12065.

14. The method of claim 4 wherein the microorganism is Actinoplanes sp. NRRL 8122 or a mutant thereof which produces the enzyme.

15. The method of claim 14 wherein the microorganism is Actinoplanes sp. NRRL 8122.

16. A method of claims 3, 4, 5, 6, 7, 8, 9, 10, 11, 12, 13, 14 or 15 wherein the enzyme is present in a culture of the producing Actinoplanaceae microorganism.

17. A method of claims 3, 4, 5, 6, 7, 8, 9, 10, 11, 12, 13, 14 or 15 wherein the antibiotic is A-30912 factor A.

18. A method of claims 3, 4, 5, 6, 7, 8, 9, 10, 11, 12, 13, 14, or 15 wherein the antibiotic is aculeacin A.

19. A method of claims 3, 4, 5, 6, or 7 wherein the antibiotic is tetrahydro-A-30912A.

20. A method of claim 16 wherein the antibiotic is A-30912 factor A.

21. A method of claim 16 wherein the antibiotic is aculeacin A.

22. A method of claim 16 wherein the antibiotic is tetrahydro-A-30912A.

* * * * *

UNITED STATES PATENT AND TRADEMARK OFFICE
CERTIFICATE OF CORRECTION

PATENT NO. : 4,293,482
DATED : October 6, 1981
INVENTOR(S) : Bernard J. Abbott and David S. Fukuda It is certified that error appears in the above—identified patent and that said Letters Patent is hereby corrected as shown below:

Column 31, lines 47-53, that part of the structural formula reading

" 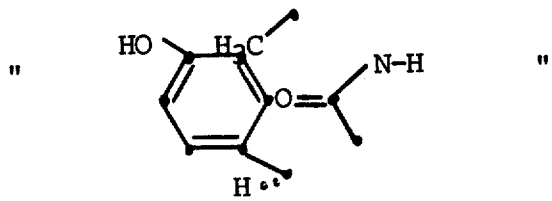 "

should read

-- 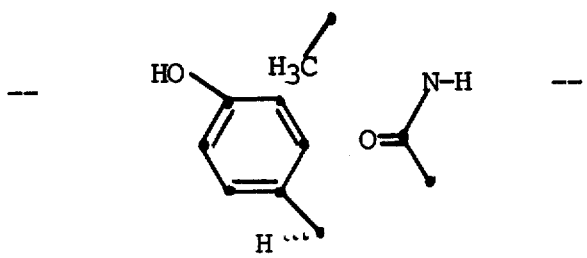 --

|SEAL|

Signed and Sealed this

Fourteenth Day of December 1982

Attest:

GERALD J. MOSSINGHOFF

Attesting Officer        Commissioner of Patents and Trademarks